US012727856B2

(12) United States Patent
Stallone et al.

(10) Patent No.: US 12,727,856 B2
(45) Date of Patent: Sep. 8, 2026

(54) ULTRASOUND TRANSDUCER FOLDING FLEX MICROELECTRONIC ASSEMBLY

(71) Applicant: GE Precision Healthcare LLC, Waukesha, WI (US)

(72) Inventors: Giandonato Stallone, Nice (FR); Alexis Hubert, Valbonne (FR); Jean-Luc Diot, Valbonne (FR); Edouard Da Cruz, Valbonne (FR)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 0 days.

(21) Appl. No.: 18/483,441

(22) Filed: Oct. 9, 2023

(65) Prior Publication Data

US 2025/0114069 A1 Apr. 10, 2025

(51) Int. Cl.
*A61B 8/00* (2006.01)

(52) U.S. Cl.
CPC .......... *A61B 8/4444* (2013.01); *A61B 8/4483* (2013.01)

(58) Field of Classification Search
CPC ............................ A61B 8/4444; A61B 8/4483
See application file for complete search history.

(56) References Cited

U.S. PATENT DOCUMENTS

| | | | | |
|---|---|---|---|---|
| 11,484,291 B2 | 11/2022 | Cuscuna | | |
| 2008/0106976 A1* | 5/2008 | Davidsen | B06B 1/0622 367/140 |
| 2011/0266042 A1* | 11/2011 | Beaman | H05K 3/403 29/829 |
| 2015/0087988 A1* | 3/2015 | Lee | B06B 1/0622 600/459 |
| 2017/0188995 A1* | 7/2017 | Bruestle | B06B 1/0685 |
| 2017/0238902 A1* | 8/2017 | Lee | A61B 8/4455 |
| 2021/0069749 A1* | 3/2021 | Durocher | B06B 1/0292 |
| 2021/0113189 A1* | 4/2021 | Bruestle | B06B 1/0685 |

FOREIGN PATENT DOCUMENTS

EP 3901677 A1 * 10/2021 ......... A61B 1/00013

* cited by examiner

*Primary Examiner* — Michael J Carey
*Assistant Examiner* — Zainab Mohammed Aldarraji
(74) *Attorney, Agent, or Firm* — McCoy Russell LLP

(57) ABSTRACT

Systems are herein provided for an ultrasound probe. In one example, an ultrasound probe comprises a housing; a transducer assembly positioned inside the housing, the transducer assembly comprising: an acoustic module; one or more printed circuit boards (PCBs); and one or more flex interconnects configured with a double bending configuration, wherein the one or more flex interconnects contact the acoustic module and the one or more PCBs.

20 Claims, 11 Drawing Sheets

ULTRASOUND TRANSDUCER FOLDING FLEX MICROELECTRONIC ASSEMBLY

FIELD

Embodiments of the subject matter disclosed herein relate to an ultrasound transducer assembly for an ultrasound probe system.

BACKGROUND

Ultrasound transducers are used extensively for ultrasound imaging of an object. Particularly, in a medical field, the ultrasound transducers are typically used to obtain a high quality image of a region within a patient. Further, this high quality image may be used for diagnosing the patient. An ultrasound transducer typically includes transducer arrays that are generally used for transmission and reception of ultrasonic or acoustic waves. These acoustic waves are further processed to obtain the image of the object. In general, transducer arrays may be flat (e.g., linear) or convex (e.g., curvilinear). Flat transducer arrays are commonly used in cardiac imaging, while convex transducer arrays are used in other diagnostic imaging applications, such as abdominal imaging.

In some examples, ultrasound transducers may include an acoustic module configured to produce and receive acoustic signals as well as one or more circuit boards configured to receive electronic signals. A shape of the ultrasound probe informs the types of imaging applications it is used for. For example, flat arrayed narrow probes are often used for cardiac imaging.

BRIEF DESCRIPTION

In one example, an ultrasound probe comprises a housing; a transducer assembly positioned inside the housing, the transducer assembly comprising: an acoustic module; one or more printed circuit boards (PCBs); and one or more flex interconnects configured with a double bending configuration, wherein the one or more flex interconnects contact the acoustic module and the one or more PCBs.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of an ultrasound probe including an ultrasound transducer assembly, and a medical imaging system including the ultrasound probe.

The ultrasound transducer assembly as herein presented includes an acoustic module connected to one or more printed circuit boards (PCBs) via one or more flex interconnects with at least double bending configurations. A method of manufacture for the ultrasound probe includes bending the one or more flex interconnects twice during assembly of the transducer assembly. The system and assembly method, with the at least double bending configuration of the flex interconnects, allows for manufacture of a compact ultrasound probe with a reduced footprint, notably in the elevation direction. Reduced footprint and dimensions may increase ergonomics and user comfort as well as increasing variety of applications for the ultrasound probe.

The disclosed ultrasound transducer assembly includes one or more PCBs aligned along an azimuthal plane with at least double bending flex interconnects connecting the one or more PCBs to an acoustic module. In some examples, the acoustic module may comprise an acoustic stack and at least one application specific integrated circuit (ASIC) which may be coupled to an acoustic backing. Each of the flex interconnects is designed to bend twice or more to allow the connection of the acoustic module to the PCBs to facilitate transmission of signals from the acoustic module to the PCBs. In a first embodiment, the flex interconnects may bend first into the elevation plane and second into the azimuthal plane. In a second embodiment, the flex interconnects may bend first into the elevation plane and second into a plane parallel to the acoustic module.

Orienting the PCBs along the azimuthal plane may allow a reduced width in the elevation plane. In this way, the transducer may be optimized ergonomically for imaging of areas with limited width, such as intercostal imaging. Further, reducing the width in the elevation direction may reduce the footprint of the handle of the probe, thereby increasing user comfort.

Figure 1:
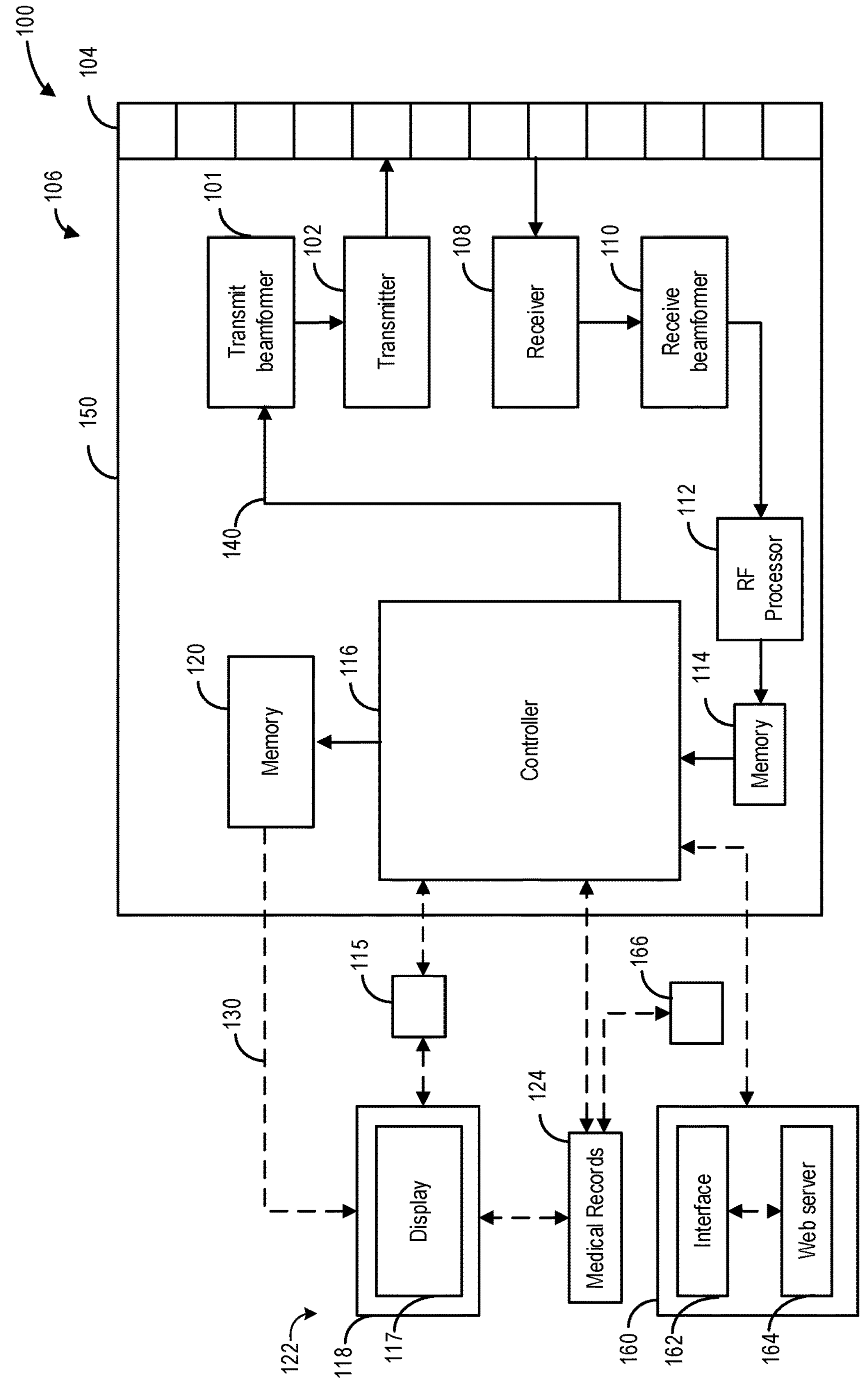
FIG. 1 shows an ultrasound imaging system according to an exemplary embodiment.
Figure 2:
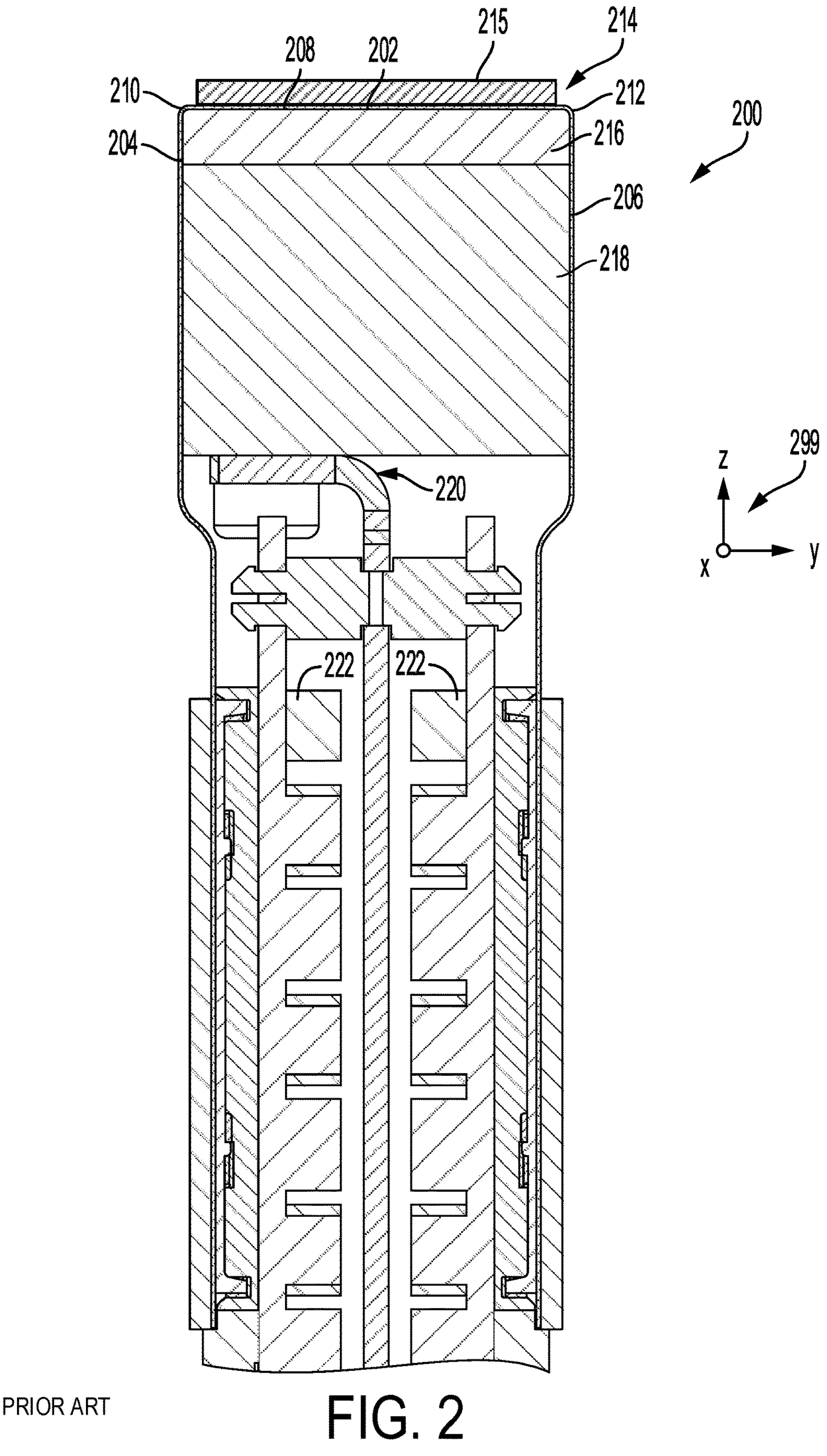
FIG. 2 shows an example conventional transducer assembly of an ultrasound probe.
Figure 3:
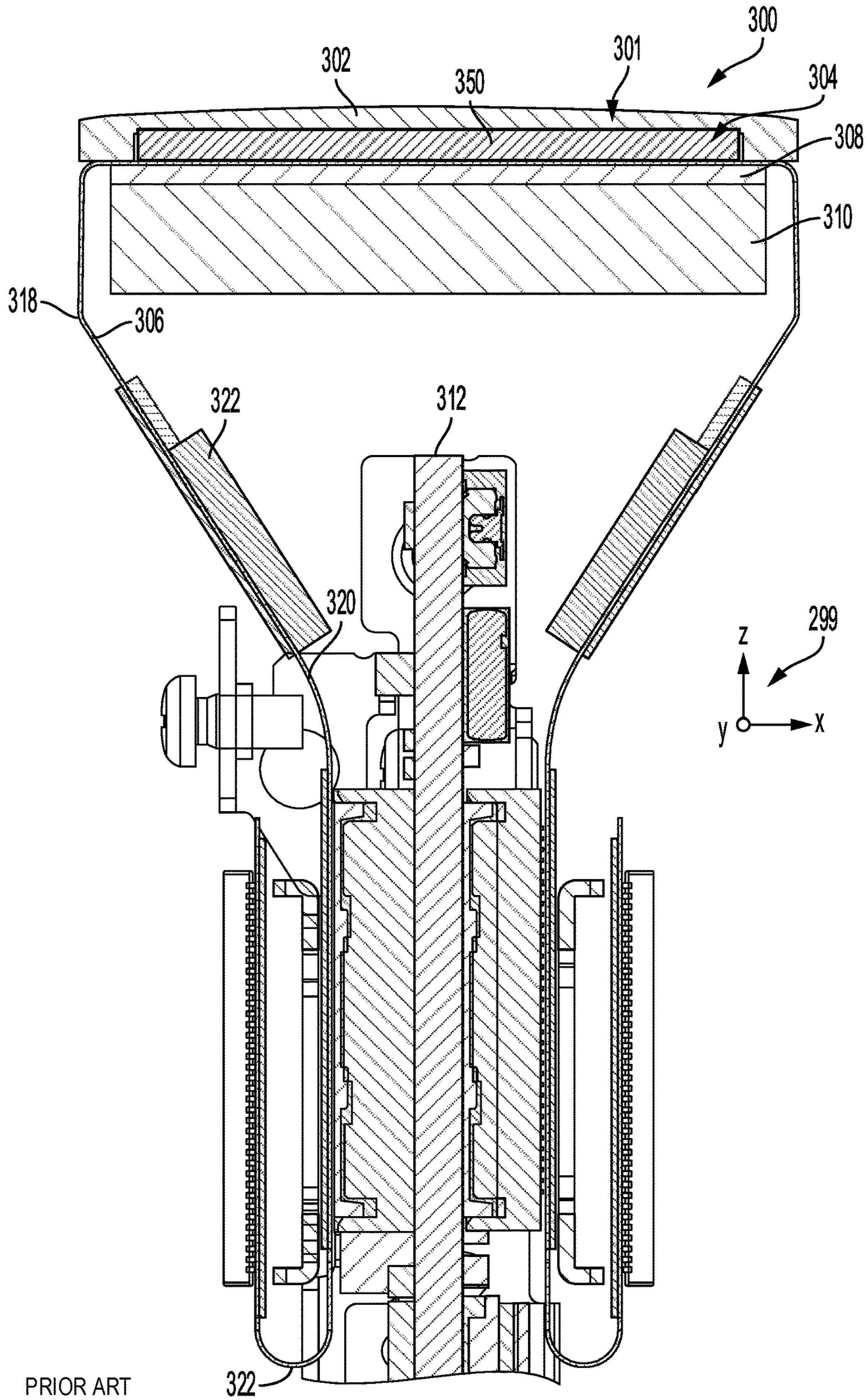
FIG. 3 shows another example conventional transducer assembly of an ultrasound probe.
Figure 4:
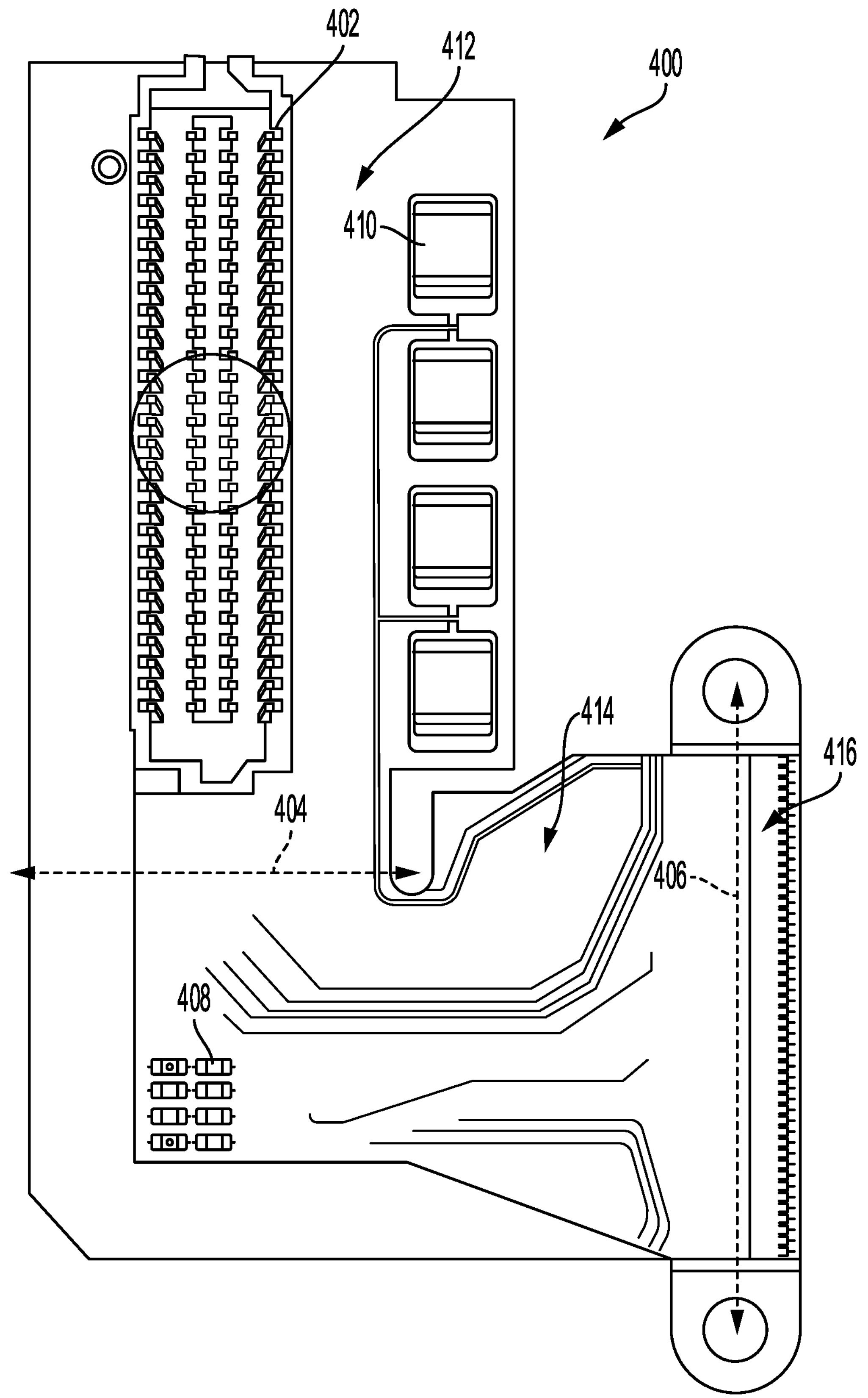
FIG. 4 shows a diagram of a first flex interconnect according to a first embodiment of the present disclosure.
Figure 5:
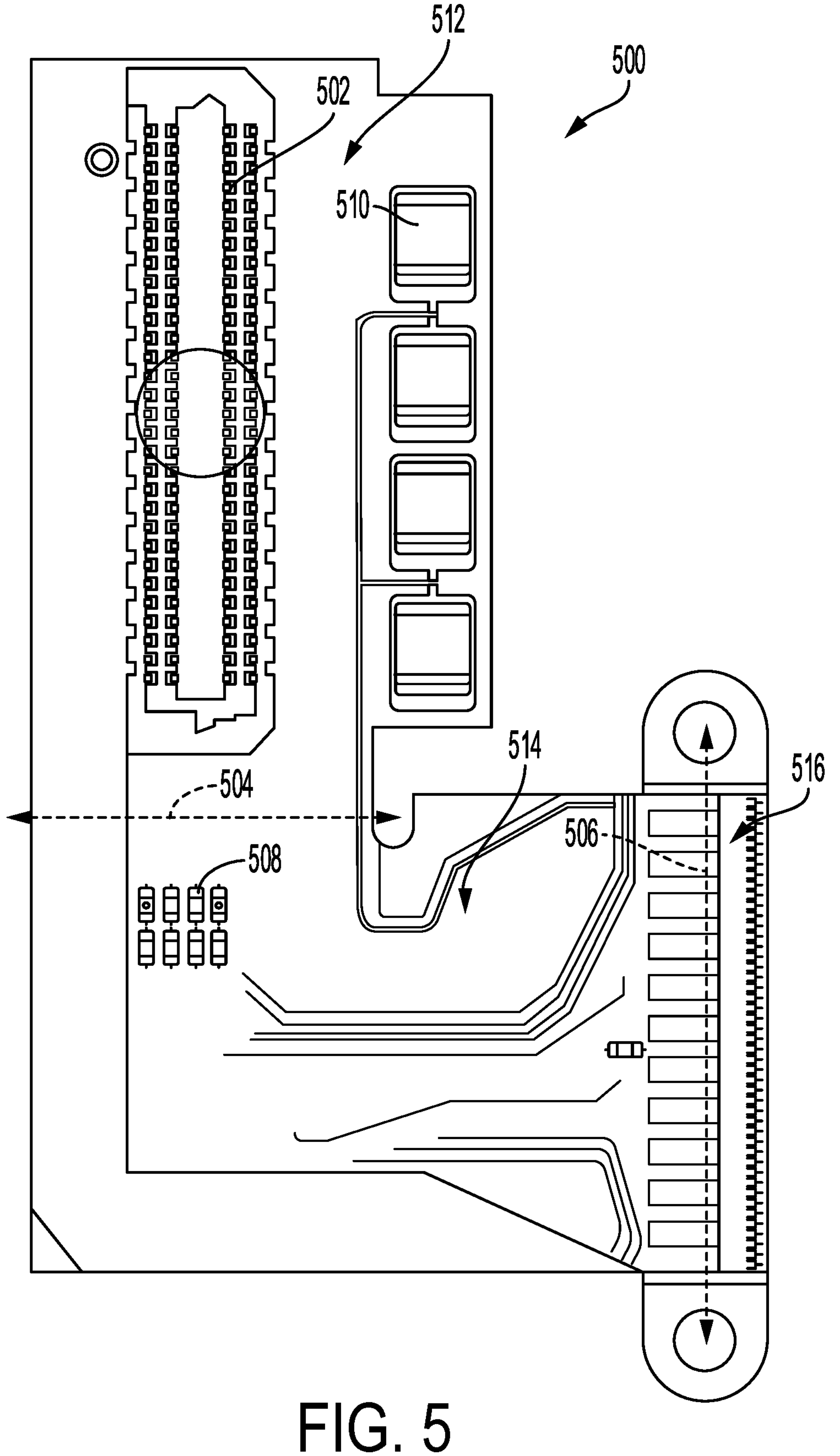
FIG. 5 shows a diagram of a second flex interconnect according to the first embodiment of the present disclosure.
Figure 6:
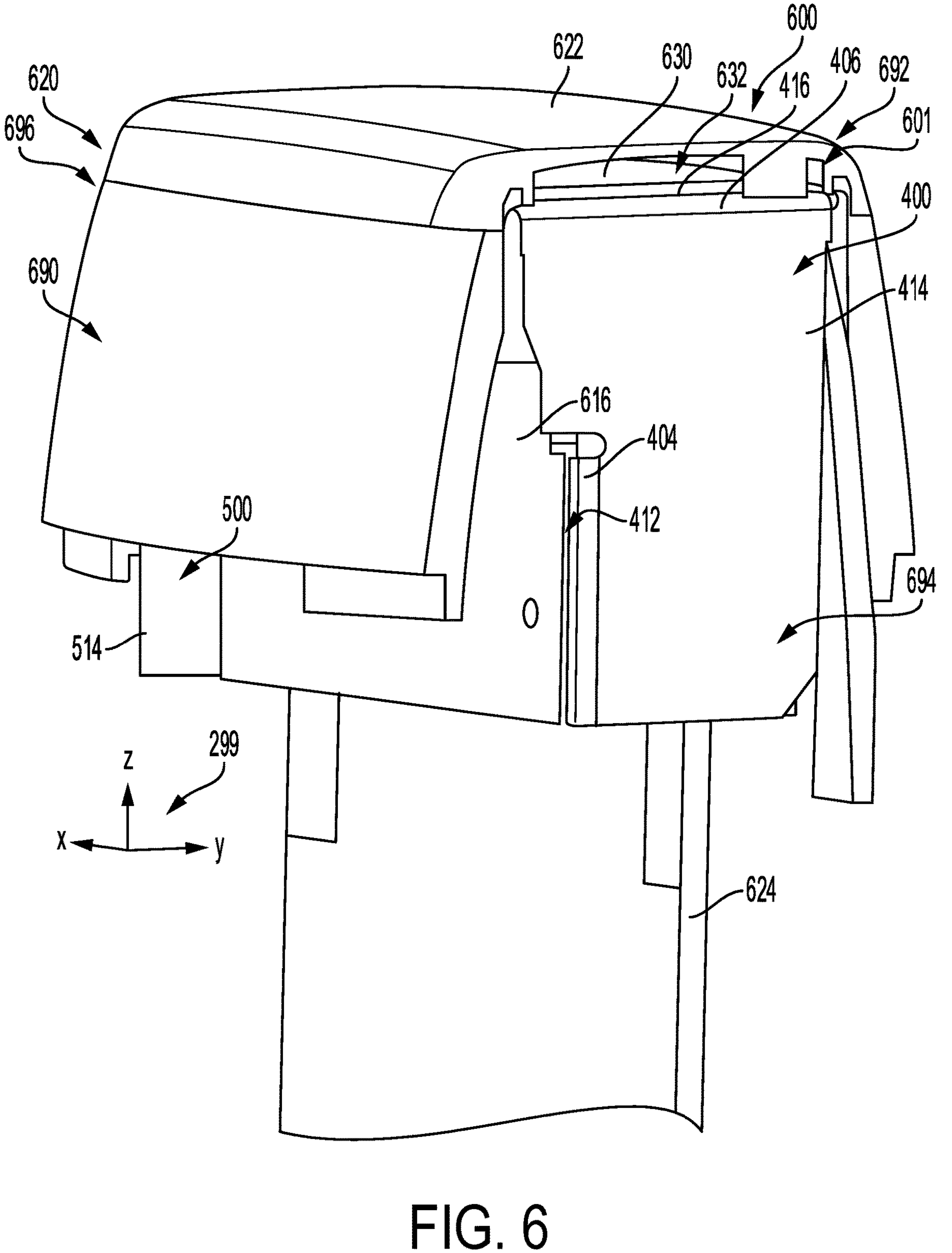
FIG. 6 shows a perspective cross-sectional view of an example ultrasound probe according to the first embodiment of the present disclosure.
Figure 7:
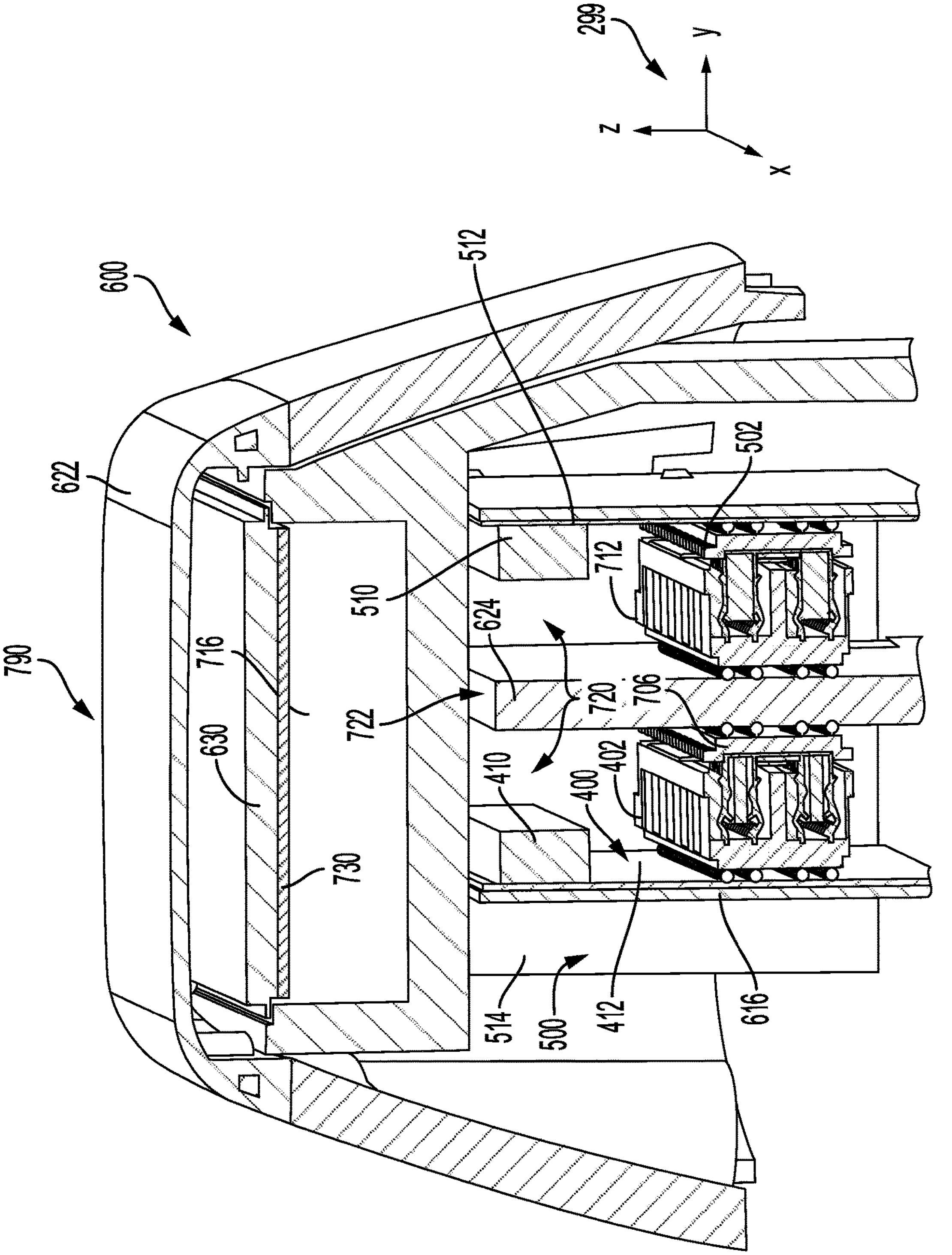
FIG. 7 shows a perspective cross-sectional view of the ultrasound probe of FIG. 6.
Figure 8:
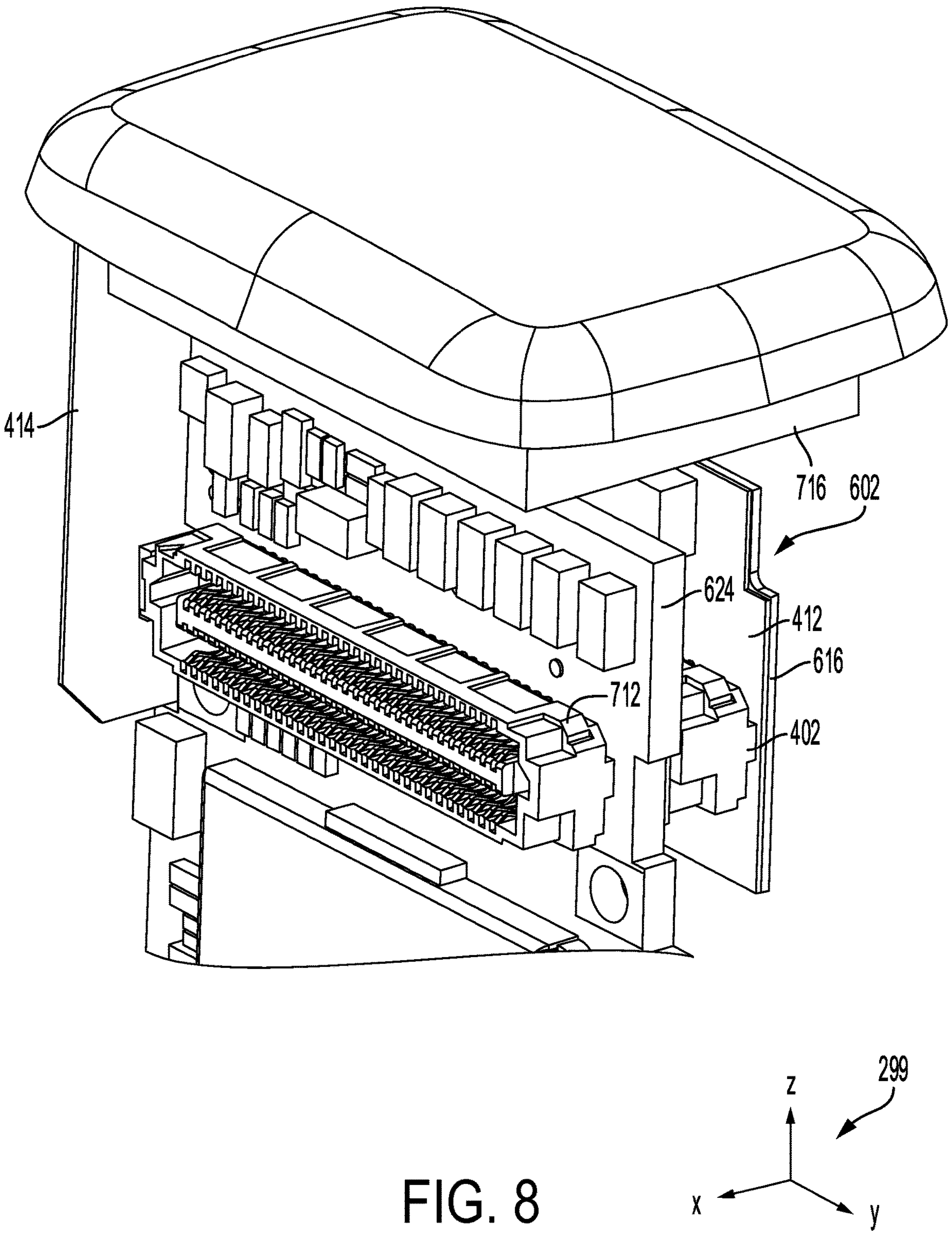
FIG. 8 shows a perspective cross-sectional view of the ultrasound probe of FIG. 6.

One example of an ultrasound imaging system including the ultrasound probe is depicted in FIG. 1. Examples of conventional transducer assemblies for ultrasound probes are shown in FIGS. 2-3. Examples of first and second flex interconnects configured with a double bending configuration are shown in FIGS. 4-5. Cross-sectional perspective views of an ultrasound probe according to a first embodiment of the present disclosure are shown in FIGS. 6-8.

Figure 9:
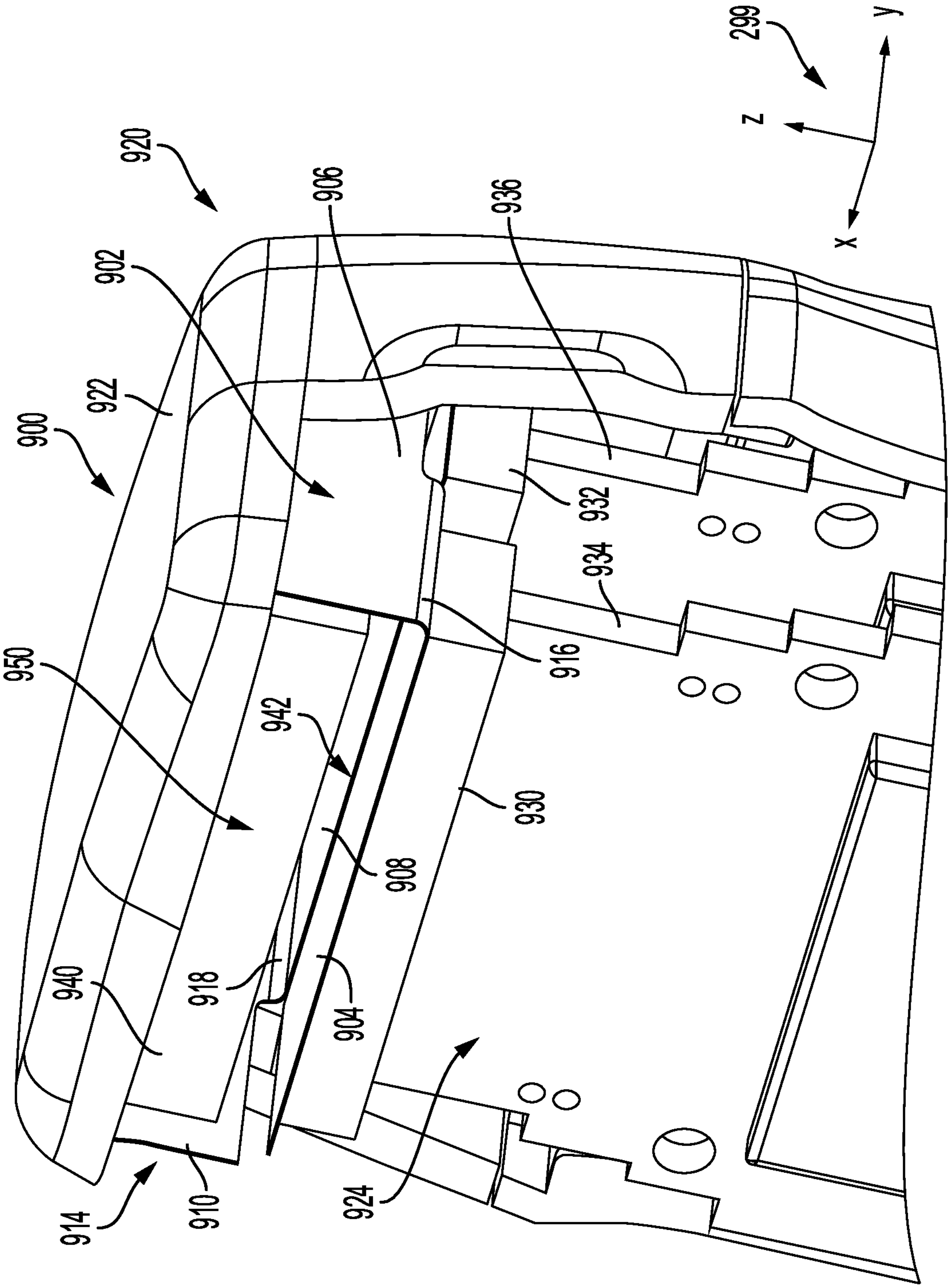
FIG. 9 shows a perspective cross-sectional view of a second example ultrasound probe according to a second embodiment of the present disclosure.
Figure 10:
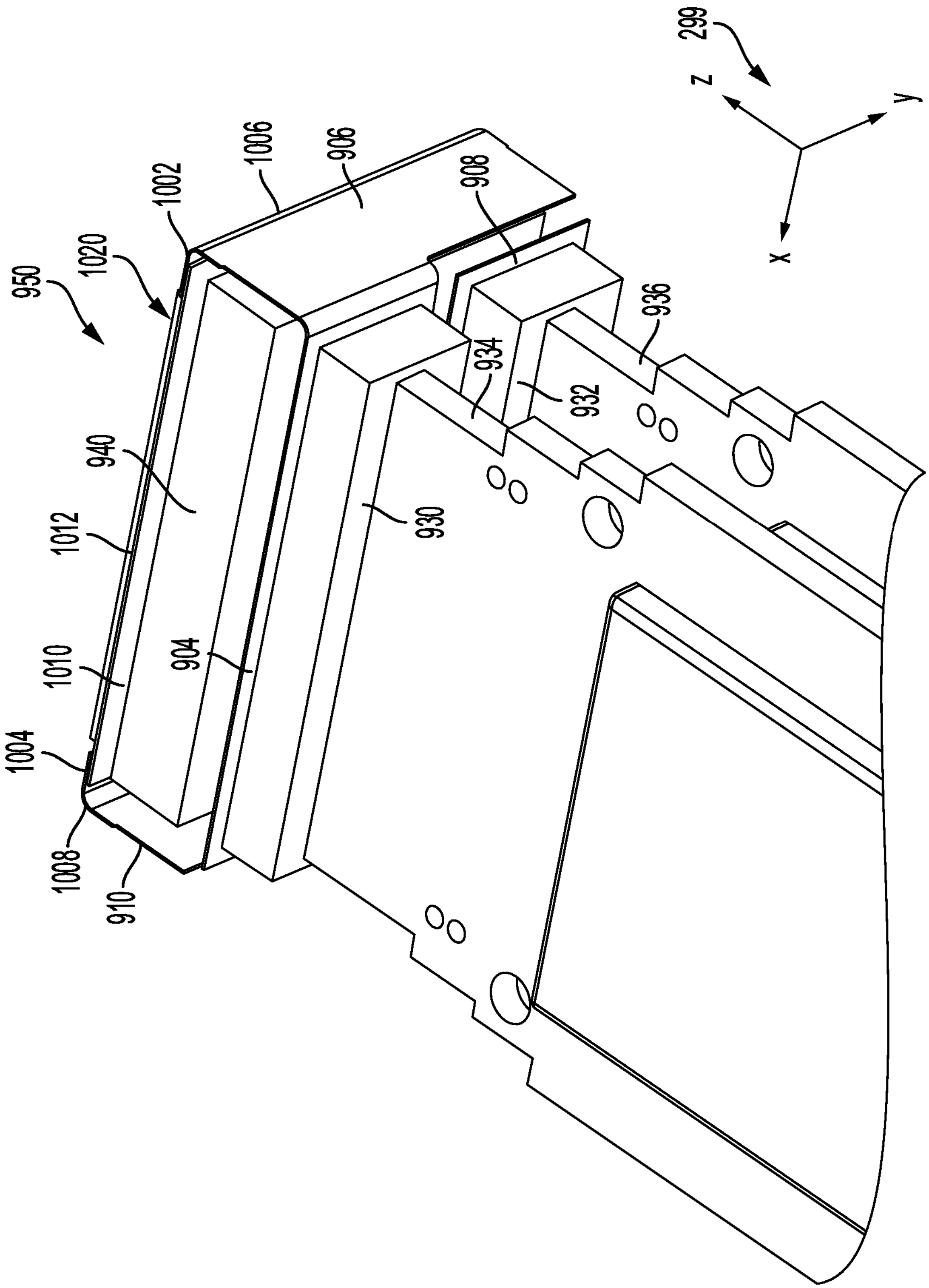
FIG. 10 shows a perspective view of a transducer assembly of the ultrasound probe of FIG. 9.

Cross-sectional perspective views of an ultrasound probe according to a second embodiment of the present disclosure are shown in FIGS. 9-10. A method of manufacture for an ultrasound probe according to the present disclosure is illustrated in a flowchart in FIG. 11.

FIGS. 2-10 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space there-between and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

FIG. 1 depicts a block diagram of a system 100 according to one embodiment. In the illustrated embodiment, the system 100 is an imaging system and, more specifically, an ultrasound imaging system. As shown, the system 100 includes an ultrasound probe 106, a user interface 122, a medical records system 124, and a remote connectivity subsystem 160. A plurality of dashed lines 130 represent communicative couplings between components of system 100. A plurality of solid lines 140 represents communicative couplings between components of ultrasound probe 106. The components may be separate but located within a common room, or may be remotely located with respect to one another. For example, one or more of the modules described herein may operate in a data server that has a distinct and remote location with respect to other components of the system 100, such as a probe and user interface.

In the illustrated embodiment, the ultrasound probe 106 comprises an ultrasound control system integrated into one or more PCBs 150 and a piezoelectric transducer comprising an array of elements 104, for example, piezoelectric elements including piezoceramics, high-dielectric ceramics, single crystals, etc. The PCBs 150 may include a controller 116 that may be part of a single processing unit (e.g., processor) or distributed across multiple processing units. The controller 116 is configured to control operation of the system 100 including, for example, image acquisition and image processing. In one example, the controller 116 of the PCBs 150 controls a transmit beamformer 101 and a transmitter 102 that drives the elements 104 within the ultrasound probe 106 to emit ultrasonic signals (e.g., continuous or pulsed) into a body or volume (not shown) of a subject. The controller 116 receives control signals from a receiver 108, a receive beamformer 110, a radio frequency (RF) processor 112, and a memory 114.

The elements 104 and the ultrasound probe 106 may have a variety of geometries. The ultrasonic signals are back-scattered from structures in a body, for example, an inserted needle, to produce echoes that return to the elements 104. The echoes are received by the receiver 108. The received echoes are provided to the receive beamformer 110 that performs beamforming and outputs a radio frequency (RF) signal. The RF signal is then provided to the RF processor 112 that processes the RF signal. Alternatively, the RF processor 112 may include a complex demodulator (not shown) that demodulates the RF signal to form I/Q data pairs representative of the echo signals. The RF or I/Q signal data may then be provided directly to the memory 114 for storage (for example, temporary storage).

For example, the controller 116 may include an image-processing module that receives image data (e.g., ultrasound signals in the form of RF signal data or I/Q data pairs) and processes image data. For example, the image-processing module may process the ultrasound signals to generate two-dimensional (2D) slices or frames of ultrasound information (e.g., ultrasound images) or ultrasound waveforms (e.g., continuous or pulse wave Doppler spectrum or waveforms) for displaying to the operator. The image-processing module may be configured to perform one or more processing operations according to a plurality of selectable ultrasound modalities on the acquired ultrasound information. By way of example, the ultrasound modalities may include color-flow, acoustic radiation force imaging (ARFI), B-mode, A-mode, M-mode, spectral Doppler, acoustic streaming, tissue Doppler module, C-scan, and elastography. Further, in some examples, the one or more processing operations may include one or more image transforms, such as a Radon transform for identifying linear features in the ultrasound images.

Acquired ultrasound information may be processed in real-time during an imaging session (or scanning session) as the echo signals are received. Additionally or alternatively, the ultrasound information may be stored temporarily in the memory 114 during an imaging session and processed in less than real-time in a live or off-line operation. An image memory 120 is included for storing processed slices or waveforms of acquired ultrasound information that are not scheduled to be displayed immediately. The image memory 120 may comprise any known data storage medium, for example, a permanent storage medium, removable storage medium, and the like. Additionally, the image memory 120 may be a non-transitory storage medium.

In operation, an ultrasound system may acquire data, for example, 2D data sets, spectral Doppler data sets, and/or volumetric data sets by various techniques (for example, three-dimensional (3D) scanning, real-time 3D imaging, volume scanning, 2D scanning with probes having positioning sensors, freehand scanning using a voxel correlation technique, scanning using 2D or matrix array probes, and the like). Ultrasound spectrum (e.g., waveforms) and/or images may be generated from the acquired data (at the controller 116) and displayed to the operator or user on a display device 118.

The controller 116 is operably connected to the user interface 122 that enables an operator to control at least some of the operations of the system 100. The ultrasound probe 106 may be communicatively coupled to the user interface 122 via one or more wireless networks. The controller 116 may also be coupled to the remote connectivity subsystem 160 including a remote connectivity interface 162 and a web server 164. Similarly, the controller 116 may be communicatively coupled to the medical records system 124 configured to receive and/or store ultrasound image data. The medical records system 124 interacts with an imaging workstation 166. Thus, transmission of data and signals between the ultrasound probe 106, the user interface 122, the medical records system 124, and the remote connectivity subsystem for generating, interpreting, and managing ultrasound images may be enabled via the one or more wireless networks. The user interface 122 may include hardware, firmware, software, or a combination thereof that enables an individual (e.g., an operator) to directly or indirectly control operation of the system 100 and the various components thereof. As shown, the user interface 122 includes the display device 118 having a display area 117. In some embodiments, the user interface 122 may also include one or more user input devices 115, such as a physical keyboard, mouse, and/or touchpad. In one embodiment, a touchpad may be configured to the controller 116 and display area 117, such that when a user moves a finger/glove/stylus across the face of the touchpad, a cursor atop the ultrasound image or Doppler spectrum on the display device 118 moves in a corresponding manner.

In an exemplary embodiment, the display device 118 is a touch-sensitive display (e.g., touchscreen) that can detect a presence of a touch from the operator on the display area 117 and can also identify a location of the touch in the display area 117. The touch may be applied by, for example, at least one of an individual's hand, glove, stylus, or the like. As such, the touch-sensitive display may also be characterized as a user input device that is configured to receive inputs from the operator (such as a request to adjust or update an orientation of a displayed image). The display device 118 also communicates information from the controller 116 to the operator by displaying the information to the operator. The display device 118 and/or the user interface 122 may also communicate audibly. The display device 118 is configured to present information to the operator during or after the imaging or data acquiring session. The information presented may include ultrasound images (e.g., one or more 2D frames), graphical elements, measurement graphics of the displayed images, user-selectable elements, user settings, and other information (e.g., administrative information, personal information of the patient, and the like).

In addition to the image-processing module, the controller 116 may also include one or more of a graphics module, an initialization module, a tracking module, and an analysis module. The image-processing module, the graphics module, the initialization module, the tracking module, and/or the analysis module may coordinate with one another to present information to the operator during and/or after the imaging session. For example, the image-processing module may be configured to display an acquired image on the display device 118, and the graphics module may be configured to display designated graphics along with the displayed image, such as selectable icons (e.g., image rotation icons) and measurement parameters (e.g., data) relating to the image.

The screen of a display area 117 of the display device 118 is made up of a series of pixels which display the data acquired with the ultrasound probe 106. The acquired data includes one or more imaging parameters calculated for each pixel, or group of pixels (for example, a group of pixels assigned the same parameter value), of the display, where the one or more calculated image parameters includes one or more of an intensity, velocity (e.g., blood flow velocity), color flow velocity, texture, graininess, contractility, deformation, and rate of deformation value. The series of pixels then make up the displayed image and/or Doppler spectrum generated from the acquired ultrasound data.

Turning now to FIGS. 2 and 3, examples of conventional transducer assemblies for ultrasound probes are shown. FIG. 2 shows a cross-sectional view of a first example of a conventional transducer assembly 200. An axis system 299 is provided for reference in FIGS. 2-10. A z-x plane may correspond to an azimuthal plane and a y-z plane may correspond to an elevation plane. The transducer assembly 200 may be included in an ultrasound probe which includes a housing (not shown) in which the transducer assembly 200 is positioned. The transducer assembly 200 comprises an acoustic module 214 (e.g., an electroacoustic module (EAM)). The acoustic module 214 may comprise an acoustic stack 215 and one or more ASICs 216. The acoustic module 214 is in contact with one or more PCBs 222 via a flex interconnect 202. The flex interconnect 202 may be positioned between the acoustic stack 215 and the ASIC 216. The transducer assembly 200 may include acoustic backing 218 positioned in contact with the ASIC 216. The acoustic backing 218 may be configured to provide isolation from ultrasonic signals. The acoustic backing 218 may further be in contact with a heat dissipation device 220. In some examples, the heat dissipation device 220 is a heat sink. The heat dissipation device 220 may be positioned on an opposite side of the acoustic backing 218 than the side coupled directly to the ASIC 216. The heat dissipation device 220 may be configured for removing heat from the transducer assembly 200 to reduce degradation and increase device performance.

The flex interconnect 202 may comprise a flat flexible electrical interconnection device comprising conductive traces within flexible insulating material. Electrical signals may be communicated between the acoustic module 214 and the one or more PCBs 222. The flex interconnect 202 may comprise one or more bends or folds across the elevation plane (e.g., from the x-y plane to the x-z plane (e.g., the azimuthal plane) to allow for contact between the acoustic module 214 and the one or more PCBs 222. In some examples, the flex interconnect 202 may comprise a first side section 206, a top section 208, and a second side section 204 opposite the first side section 206. A first bend 212 may transition between the first side section 206 and the top section 208 and a second bend 210 may transition between the top section 208 and the second side section 204.

The one or more PCBs 222 of the transducer assembly 200 may be oriented along the azimuthal plane. A size of the one or more PCBs 222 of the ultrasound probe define a size of a handle of the probe along the azimuthal direction. The width of the ultrasound probe (e.g., along the y-axis) may be a limiting factor for application of the probe. The single bend across the elevation plane for each side and the contact with the one or more PCBs along a large portion of the z-axis may result in a wider width of the probe than is usable for certain applications, such as cardiac approaches demanding intercostal imaging.

FIG. 3 shows a cross-sectional view of a second example of a conventional ultrasound probe 300. The ultrasound probe 300 includes a housing, including a lens 302, positioned around a transducer assembly 301. In some examples, the transducer assembly 301 includes an acoustic module 304 that comprises an acoustic stack 350 and an ASIC 308.

A flex interconnect 306 may be positioned between and in contact with the acoustic stack 350 and the ASIC 308 and may be configured to transmit received signals from the acoustic stack 350 and/or the ASIC 308 to one or more PCBs 312. The ASIC 308 may be in further contact with an acoustic backing 310 on an opposite side from the flex interconnect 306. The acoustic backing 310 may be configured for isolating the acoustic signals.

The flex interconnect 306 may comprise a plurality of bends or folds to allow for contact with the one or more PCBs 312 of the transducer assembly 301. For example, on both a first and a second side, the flex interconnect 306 may comprise a first bend 318, a second bend 320, and a third bend 322. The first and second bends may form obtuse angles while the third bend may comprise a 180 degree turn. The one or more PCBs 312 of the ultrasound probe 300 may be oriented along the elevation plane. A width of the elevation plane may be defined by a size of the one or more PCBs 312 in the elevation direction. The width of the ultrasound probe 300 in the elevation direction may be smaller than a length in the azimuthal direction.

With the one or more PCBs aligned parallel to the elevation plane, a size or compactness the size of the one or more PCBs 312 may be configured for an application of the ultrasound probe 300, for example for intercostal imaging, and thus may be smaller than ideal or practical to allow for intercostal imaging and maintain user comfort and hand grip.

An ultrasound probe is herein presented with one or more double folding flex interconnects that allow for contact between an acoustic module and one or more PCBs positioned along the azimuthal plane while retaining a small elevation aperture as may be used for specific applications like intercostal imaging. The at least double bending configuration of the one or more flex interconnects may also increase a number of surfaces available for heat transfer and reduction may be available as well. The bending configuration is herein described as double, though it should be understood that more than two bends are possible and the bending configuration is at least a double bending configuration.

Turning now to FIGS. 4 and 5, a first flex interconnect 400 and a second flex interconnect 500 that may be included in a transducer assembly according to a first embodiment of the present disclosure are shown, respectively. The first and second flex interconnects 400, 500, may be flat flexible electrical interconnection devices comprising conductive traces within flexible insulating material The first and second flex interconnects 400, 500 may be included in a transducer assembly of an ultrasound probe, such as will be explained further with respect to FIGS. 6-8. The first and second flex interconnects 400, 500 are shown in FIGS. 4 and 5, respectively, in an unfolded state, and are shown in a folded state in FIGS. 6-8.

In some examples, the first and second flex interconnects 400, 500, as well as other flex interconnects herein described, may be made of a thin layer of polymide or any other type of plastic that may withstand high temperatures and is highly resistant to chemicals and radiation. In some examples, a circuit may then be printed onto the polymide layer using copper traces or conductive ink, which form the electrical traces.

The first flex interconnect 400 may comprise a plurality of bends, including a first bend 404 and a second bend 406. The first bend 404 may transition between a first section 412 and a second section 414. The second bend 406 may transition between the second section 414 and a third second 416. The first section 412 may comprise a first connector 402 and one or more capacitors 410, in some examples. The capacitors 410 may be configured for electrical decoupling. In other examples, capacitors may not be present. The first connector 402 may be configured to couple to a connector of a PCB to which the flex interconnect 400 contacts within an ultrasound probe. In some examples, the second section 414 may comprise passive components 408, such as capacitors, resistors, inductors, diodes, thermistors, etc., though in other examples the passive components may not be present.

The second flex interconnect 500 may comprise a similar plurality of bends, including a first bend line 504 and a second bend line 506. The first bend line 504 may transition between a first section 512 and a second section 514. The second bend line 506 may transition between the second section 514 and a third section 516. The first section 512 may comprise a second connector 502 and capacitors 510, in some examples. In other examples, the capacitors 510 may not be present. The second connector 502 may be configured to couple to a connector of a PCB to which the flex interconnect 500 contacts within an ultrasound probe. The second section 514 may comprise a passive components 508, such as capacitors, resistors, inductors, diodes, thermistors, etc., in some examples. In other examples, the passive components 508 may not be present. In some examples, when assembled, each of the bends herein described may be 90 degrees. In other examples, the bends may have varying angles.

In some examples, the passive components 408 of the first flex interconnect may be positioned closer to the first bend 404 than the passive components 508 of the second flex interconnect is to the first bend 504. In this way, the two flex interconnect design may allow for connection to a PCB that is not centered within the transducer assembly. In other examples, the passive components of each flex interconnect may be positioned the same when the PCB is centered or may not be present.

Relative positioning of the first and second flex interconnects 400, 500, when assembled, within an ultrasound probe is shown in FIGS. 6-8, and as such similar component numbering is used. FIG. 6 shows a cross-sectional perspective view of an ultrasound probe 600. The ultrasound probe 600 comprises a nosepiece 620 in which a transducer assembly 601 is housed. The nosepiece 620 may include a lens 622. When packaged, the lens 622 may be positioned over a top (e.g., with respect to the z-axis) of the transducer assembly 601 and may be configured for contacting a patient being imaged.

The transducer assembly 601 may comprise one or more flex interconnects, including the first flex interconnect 400 and the second flex interconnect 500. As previously described, the first and second flex interconnects 400, 500 may be flat flexible electrical interconnection devices comprising conductive traces within flexible insulating material. The first and second flex interconnects 400, 500 may be positioned and configured to contact an acoustic module 632. In some examples, the acoustic module 632 is an EAM comprising an acoustic stack 630 and/or one or more ASICs (not shown). The acoustic stack 630, and other acoustic stacks herein described, may comprise an array of piezoelectric elements configured to produce and/or receive acoustic signals entering or exiting a patient being imaged. The first and second flex interconnects 400, 500 may be further positioned and configured to contact one or more PCBs 624 due to the double bending configuration. In some examples, the first flex interconnect 400 may be the first flex interconnect 400 described with respect to FIG. 4 and the second flex interconnect 500 may be the second flex interconnect 500 described with respect to FIG. 5. Each of the first and second flex interconnects 400, 500 may be backed by a stiffener for structure, such as stiffener 616.

The one or more PCBs 624, as well as other PCBs of transducer assemblies herein described, may comprise single-sided boards, double-sided boards, or multi-layered boards. In one example, the one or more PCBs 624 may comprise the main circuit board of the ultrasound control system described with reference to FIG. 1. For example, the one or more PCBs 624 may include one or more of transmitter and receiver channels for generating and processing ultrasound signals, analog-to-digital converters for converting the analog transducer signals into digital signals, digital circuitry for performing beamforming, filtering, and other algorithms for processing the ultrasound data, memory including RAM and/or flash memory, Complex Programmable Logic Devices (CPLD), and control circuitry including one or more microcontrollers.

Similar to as described with respect to FIG. 4, the first flex interconnect 400 may be partitioned into a first section 412, a second section 412, and a third section 416, with a first bend 404 transitioning between the first section 412 and the second section 412 and a second bend 406 transitioning between the second section 412 and the third section 416. The second flex interconnect 500, while not shown in FIG. 6, may be partitioned and bent similarly. The first section 412 may be positioned parallel to the azimuthal plane (e.g., the x-z plane). The second section 412 may be positioned parallel to the elevation plane (e.g., the y-z plane). The third section 416 may be positioned parallel to the x-y plane (e.g., parallel with the acoustic module 632). In some examples, each of the first and second bends 404, 406 may be 90 degree bends when the transducer assembly 601 is assembled such that each of the first, second, and third sections 412, 414, and 416 may be perpendicular to each of the other sections. In this way, the first and second flex interconnects 400, 500 may allow for connection between the acoustic module 632 in a first direction (e.g., of the x-y plane) to the one or more PCBs 624 in a second direction (e.g., of the azimuthal plane), which may reduce the footprint and/or aperture in the elevation direction. Further, the double bending configuration may allow for an increased number of surfaces of the flex interconnect are available, for example for heat transfer and/or dissipation purposes.

The first section 412 may be positioned towards a first side 690 of the ultrasound probe 600. The second section 412 may be positioned towards a first end 694 of the ultrasound probe 600, wherein the first end 694 is adjacent in a perpendicular manner to the first side 690. The first section 512 of the second flex interconnect 500, which is not well visualized in FIG. 6, may be positioned towards a second side 692 opposite the first side 690 and the second section 514 of the second flex interconnect 500 may be positioned towards a second end 696 opposite the first end 694. The third section 416 of the first flex interconnect 400 and the third section 516 of the second flex interconnect 500, which is not well visualized in FIG. 6, may both be positioned towards the lens 622, parallel with and in contact with the acoustic module 632. Each of the third sections may be positioned at a lateral edge of the acoustic module 632. In this way, the first and second flex interconnects 400, 500 may both provide contact between the acoustic stack 630 and/or one or more ASICs and one or more PCBs 624 without increasing the footprint in either the elevation or azimuthal directions by allowing contact across different planes. The first section 412 may be parallel to and in contact with the stiffener 616 which may be positioned along the azimuthal plane and towards the first side 690. In some examples, another backing may be positioned towards the second side 692 and may be parallel to and in contact with the first section 512 of the second flex interconnect 500.

The third section 416 of the first flex interconnect 400 may be positioned in the same x-y plane as the third section 516 of the second flex interconnect 500, with the third section 416 being positioned towards the first end 694 and the third section 516 of the second flex interconnect 500 being positioned towards the second end 696. By positioning the respective corresponding sections of the first and second flex interconnects 400, 500 opposite each other within the ultrasound probe 600, the number of available surfaces is increased, both for heat transfer and for contact with ASICs and PCBs.

At least one PCB 624 may be included in the transducer assembly 601. The at least one PCB 624 may be positioned parallel to the azimuthal plane, and therefore may be parallel to the first section 412 of the first flex interconnect 400 (and to the first section of the second flex interconnect 500 not visualized in FIG. 6) when the transducer assembly 601 is assembled. The at least one PCB 624 may be positioned between the first sections along the y-axis. Each of the first and second flex interconnects 400, 500 may be oriented such that respective connectors may face inwards towards the at least one PCB 624, as will be seen with respect to FIG. 7.

Turning now to FIG. 7, another cross-sectional perspective view of the ultrasound probe 600 according to the first embodiment of the present disclosure is shown. The second flex interconnect 500 may comprise the first section 512, the second section 514, and the third section 516, which is not well visualized in FIG. 7. Similar to as described with respect to FIGS. 4-6, the first flex interconnect 400, specifically the first section 412 of the first flex interconnect 400, may comprise the first connector 402. Similarly, the second flex interconnect 500, specifically the first section 512, may comprise the second connector 502. The first connector 402 may be configured to couple to a first corresponding connector 706 of the at least one PCB 624. The second connector 502 may be configured to couple to a second corresponding connector 712 of the at least one PCB 624. The first and second connectors 402, 502 may be configured with different shapes to connect to the first and second corresponding connectors 706, 712, respectively, which have different shapes from each other. In this way, the first and second flex interconnects 400, 500 and the at least one PCB 624 may be configured to assemble more efficiently. Further, the differing shapes may act as poka-yokes to prevent or avoid assembly mistakes. As an example, the first and second connectors 402, 502 and the corresponding connectors 706, 712 may be mezzanine connectors.

When present, in some examples, the capacitors 410 and 510 may be positioned so as to have open spaces 720 between the capacitors and the at least one PCB 624 when the transducer assembly 601 is assembled. Further, the open spaces 720 are facilitated by the double folding configuration of the first and second flex interconnects 400, 500, whereby the second sections 414, 514 are spaced apart from each other on opposing sides along the azimuthal direction, allowing the open spaces 720 therebetween.

The ultrasound probe 600 may further comprise the acoustic stack 630. The acoustic stack 630 may be in contact with the first and second flex interconnects 400, 500 at the third section 416 of the first flex interconnect 400 and the third section 516 of the second flex interconnect 500. In some examples, the first and second flex interconnects 400, 500 may be in further contact with an ASIC 730 such that the third sections 416, 516 of the first and second flex interconnects 400, 500 are positioned directly between the acoustic stack 630 and the ASIC 730. The ASIC 730 may be in further contact with an acoustic backing 716 on an opposite side than contacts the third sections of the flex interconnects. For example, a bottom side of the ASIC 730 may contact the acoustic backing 716 and a top side of the ASIC 730 may contact the flex interconnects. The first and second flex interconnects 400, 500 may be positioned between the acoustic stack 630 and the ASIC 730, for example a top surface of the third sections of the first and second flex interconnects 400, 500 may be in face sharing contact with a bottom surface of the acoustic stack 630 and a bottom surface of the third sections 416, 516 of the first and second flex interconnects 400, 500 may be in face sharing contact with a top surface of the ASIC 730. In this way, contact may be maintained between the flex interconnects and the acoustic module and the acoustic backing may more readily impede and/or absorb acoustic waves produced by the acoustic module. As is seen in FIG. 7, a clearance 722 may be present between the bottom surface of the acoustic backing 716 and the first and second portions of the first and second flex interconnects 400, 500 to allow for space for tolerances and/or placement of heat dissipation devices (e.g., heat spreaders, heat pipes, etc.).

FIG. 8 shows the one or more PCBs 624 from a perspective view of the second side 692 and second end 696. The one or more PCBs 624 may be configured to be positioned within the probe 600 and connected to the first and second flex interconnects 400, 500 in only one direction. For example, the first corresponding connector 706 of the PCB 624 may be configured to couple to the first connector 402 of the first flex interconnect 400 but not to the second connector 502 of the second flex interconnect 500. In this way efficiency of assembly may be increased.

The double bending configuration of each of the first and second flex interconnects may increase a number of available surfaces for heat dissipation. As discussed, the double bending configuration may allow for the clearance 722, which increases space lateral to and underneath (e.g., below the bottom surface of) the backing 716 where heat exchangers may be mounted. This may reduce any increase in footprints that would result from adding heat dissipation devices to outer facing aspects, especially in the elevation direction.

Each of the flex interconnects, and the placement of the flex interconnects within the probe, may be configured to reduce a footprint along the elevation plane while maintaining contact between the acoustic module and the one or more PCBs. In some examples, reduced footprints in the elevation direction may allow for usage of the ultrasound probe 600 in a wider variety of applications. As an example, for imaging scenarios demanding intercostal placement of the lens 622 of the ultrasound probe 600, such as for cardiac ultrasound imaging, the footprint of the probe 600 in the elevation direction is directly related to ability to place the ultrasound probe 600 to image through an intercostal space. Further, the footprint in the azimuthal direction may be directly correlated to the one or more PCBs positioned along the azimuthal direction, and the one or more PCBs may be chosen for user comfort and ergonomics. In this way, the double bending configuration of the flex interconnects allows the footprint of the probe 600 to be optimized for usage, comfort, and ergonomics while maintaining heat transfer capability and acoustic modulation.

It should be understood that while the transducer assembly 601 is herein described as including two flex interconnects, the transducer assembly 601 may include only one flex interconnect, in some examples. For example, the third sections 416 and 516 may be formed as part of the same section such that a single flex interconnect with two sides, each of the two sides having an at least double bending configuration, is present. As another example, a transducer assembly with one flex interconnect with a single wing with an at least double bending configuration has been contemplated.

Further, as previously noted, it should be understood that while a double bending configuration is herein described, in some examples the flex interconnect(s) may comprise more than two bends, such as a triple bending configuration. The bends may be 90 degrees or other suitable angle as previously described.

Turning now to FIGS. 9 and 10, an ultrasound probe 900 according to a second embodiment of the present disclosure is shown. FIG. 9 shows the ultrasound probe 900 from a cross-sectional perspective view illustrating position of one or more PCBs within a housing. FIG. 10 shows the ultrasound probe 900 from a cross-sectional perspective view illustrating configuration and position of one or more interconnects.

Similar to the ultrasound probe 600, the ultrasound probe 900 comprises a transducer assembly 950 housed within a nosepiece 920. The housing 920 may comprise a lens 922 configured to contact a patient during image acquisition. The transducer assembly 950 may comprise one or more interconnects configured with a double bending configuration, in some examples two flex interconnects. For example, the transducer assembly 950 comprises a first flex interconnect 902 and a second flex interconnect 914. The first flex interconnect 902 may comprise a first section 904, a second section 906, and a third section 1002, wherein a first bend 916 transitions between the first section 904 and the second section 906 and a second bend 1006 transitions between the second section 906 and the third section 1002. The second flex interconnect 914 similarly may comprise a first section 908, a second section 910, and a third section 1004, wherein a first bend 918 transitions between the first section 908 and the second section 910 and a second bend 1008 transitions between the second section 910 and the third section 1004.

The third sections 1002, 1004 of the first and second flex interconnects 902, 914, respectively, may both contact an acoustic module 1020. The acoustic module 1020 may comprise an acoustic stack 1012 and an ASIC 1010, in some examples. The lens 922 of the nosepiece 920 may be positioned over (e.g., covering) the acoustic module 1020 and may be positioned against a patient in order for the acoustic module to transmit produced ultrasound signals through the patient and receive ultrasonic signals. The third sections 1002, 1004 may be positioned between the acoustic stack 1012 and the ASIC 1010. The first sections 904, 908 of the first and second flex interconnects 902, 914, respectively, may each comprise a connector, for example the first section 904 may comprise a first connector 930 and the first section 908 may comprise a second connector 932. The first and second connectors 930, 932 may be configured to connect to one or more PCBs 924. As an example, the first connector 930 may be configured to connect to a first PCB 934 and the second connector 932 may be configured to connect to a second PCB 936. The first and second flex interconnects 902, 914 may be configured to communicate signals from the acoustic stack 1012 and/or the ASIC 1010 to the one or more PCBs 924. The first and second connectors 930, 932 may comprise edge board connectors, 90 degree board to board connectors, or the like, to directly transmit signals from the acoustic module 1020 to the one or more PCBs. In some examples, each edge board connector may be configured to couple to a corresponding PCB.

The first sections 904, 908 may be parallel with the acoustic module 1020, e.g., parallel with the x-y plane while the one or more PCBs 924 to which the first sections 904, 908 are connected via the first and second connectors 930, 932, respectively, are positioned along the azimuthal plane (e.g., the x-z plane). The flex interconnects may therefore contact the acoustic module in a first plane and connect to the one or more PCBs in a second plane, wherein the second plane is perpendicular to the first plane. In this way, the footprint in the elevation direction (e.g., along the y-z plane) may be reduced. In some examples, a reduced elevation aperture and footprint may allow for usage of the ultrasound probe 900 in applications that demand a small elevation footprint, such as intercostal imaging applications. The double bending configuration of the first and second flex interconnects 902, 914 may thus allow for direct connection between the acoustic module 1020 and the one or more PCBs 924 without unduly increasing either the elevation footprint or the azimuthal footprint. In this way, user comfort and ergonomics may be optimized as well as increasing usability for a variety of applications.

Further, an acoustic backing 940 may be positioned directly underneath and in contact with the ASIC 1010 to provide isolation from produced ultrasonic signals. The acoustic backing 940 may be separated from the first sections 904, 908 by a clearance 942 to allow for placement of a heat dissipation/transfer device (e.g., a heat sink) during assembly as previously described. The double bending configuration of the first and second flex interconnects 902, 914 with the second sections 906, 910 providing separation may allow for placement of such devices, thereby allowing for increased cooling and decreased degradation to the assembly.

Similar to as described above, it should be understood that while the transducer assembly 950 is herein described as including two flex interconnects, the transducer assembly 950 may include only one flex interconnect, in some examples. For example, the third sections 1002 and 1004 may be formed as part of the same section such that a single flex interconnect with two sides, each of the two sides having a double bending configuration, is present. As another example, a transducer assembly with one flex interconnect with a single wing with two or more bends has been contemplated.

Figure 11:
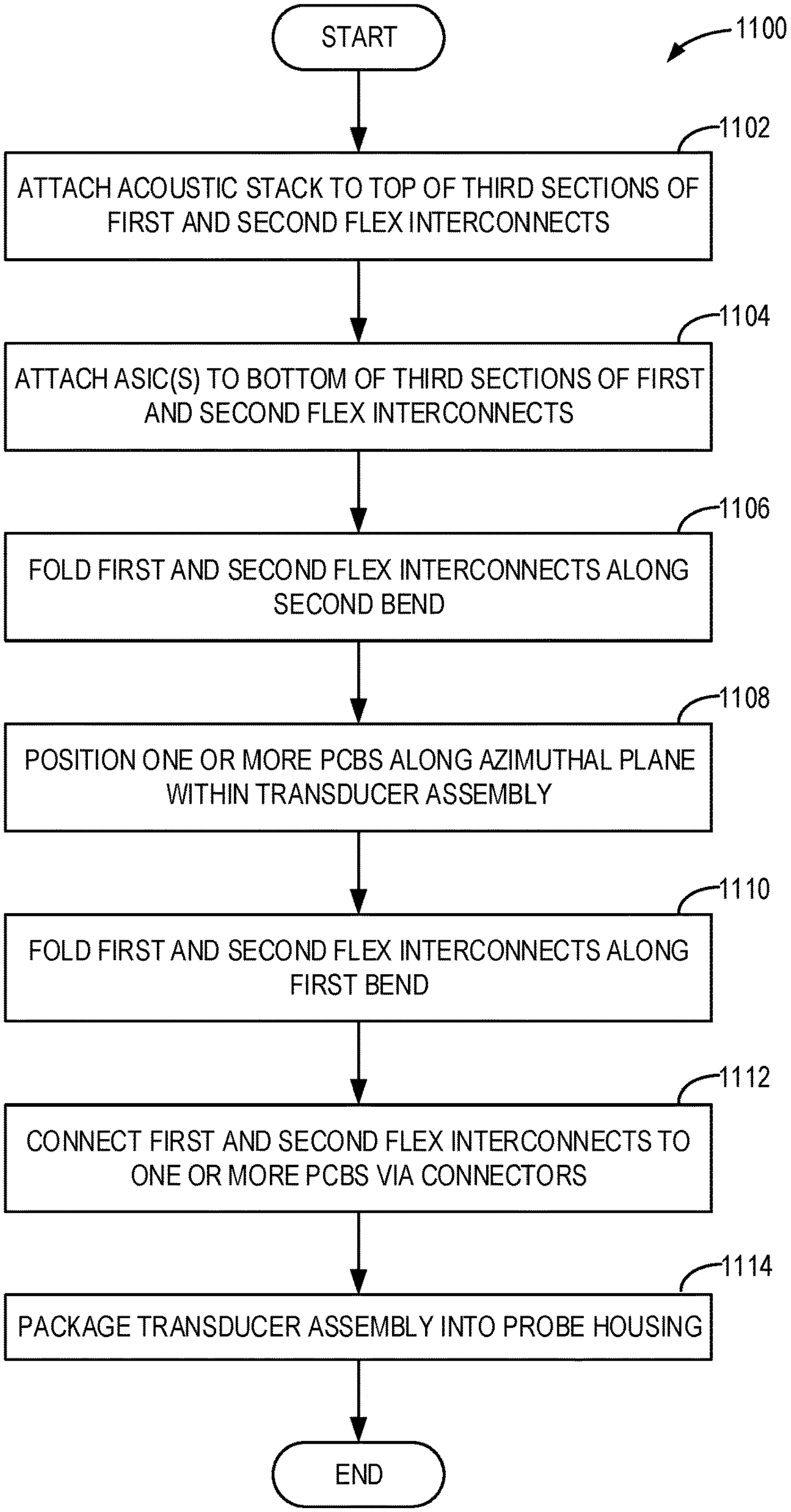
FIG. 11 is a flow chart illustrating a method of manufacture for an ultrasound probe including a transducer assembly with two flex interconnects.

FIG. 11 shows a flowchart illustrating a method 1100 for manufacturing an ultrasound probe including double folding of flex interconnects during assembly. The method 1100 is described with regard to either the first or second embodiments described above with respect to FIGS. 6-10, however it should be appreciated that method 1100 may be implemented to manufacture other examples without departing from the scope of this disclosure.

At 1102, method 1100 may include attaching an acoustic stack to a top of each third section of a first and second flex interconnects. The top in this instance may indicate an aspect of the third sections that is positioned facing a lens of a nosepiece of the ultrasound probe. In some examples, a first side of the acoustic stack may be attached to the third section of the first flex interconnect and a second side of the acoustic stack may be attached to the third section of the section flex interconnect, wherein the first and second sides are opposite one another along an azimuth direction (e.g., the x-axis of axis system 299).

At 1104, method 1100 may include attaching one or more ASICs to a bottom of each third section of the first and second flex interconnects. The bottom in this instance may indicate an aspect of the third sections that are positioned facing away from the nose of the housing of the ultrasound probe. In this way, the one or more ASICs may be positioned on an opposite side of the third sections from the acoustic stack. The third sections of the first and second flex interconnects may therefore be parallel to the acoustic module and positioned directly between and in contact with the acoustic stack and the one or more ASICs.

At 1106, method 1100 may include folding each of the first and second flex interconnects 90 degrees along respective second bends. The second bends as herein referenced may be the second bends of the first flex interconnect of the ultrasound probe 600 and the ultrasound probe 900 (e.g., second bend 406 and second bend 1006) and of the second flex interconnect of ultrasound probe 600 and ultrasound probe 900 (e.g., second bend 1008). Folding each of the first and second flex interconnects 90 degrees along respective second bends may result in second sections of each of the first and second flex interconnects being parallel to an elevation plane (e.g., the y-z plane of axis system 299) and perpendicular to the acoustic module.

At 1108, method 1100 may include positioning one or more PCBs along an azimuthal plane (e.g., the x-z plane of axis system 299). Positioning the one or more PCBs may comprise positioning the one or more PCBs below the one or more ASICs within the transducer assembly. The one or more PCBs may be aligned along the z-axis to match position of connectors along the z-axis of the first and second flex interconnects.

At 1110, method 1100 may include folding each of the first and second flex interconnects 90 degrees along respective first bends. In some examples, the first bends may be the first bends of the first flex interconnect of the ultrasound probe 600 or ultrasound probe 900 (e.g., the first bend 404 or the first bend 916) and of the second flex interconnect of the ultrasound probe 600 or the ultrasound probe 900 (e.g., first bend 918). In manufacture of the ultrasound probe according to the first embodiment, the one or more PCBs may be positioned prior to, or in some examples following, folding at the first bends. In manufacture of the ultrasound probe according to the second embodiment, the one or more PCBs may be positioned following folding at the first bends. In some embodiments, as is described with respect to FIGS. 6-8, folding along respective first bends at 90 degrees may result in respective first sections being parallel to the azimuthal plane. In other embodiments, as is described with respect to FIGS. 9-10, folding along respective first bends at 90 degrees may result in the first sections being parallel to the third sections and the acoustic module.

While it is herein described that the first and second flex interconnects may be folded along respective first bends and/or respective second bends at the same time, it should be understood that the first flex interconnect may be folded along its first and second bend prior to or following the second flex interconnect being folded along its first and second bed. Further, it should be understood that the first bends may be folded prior to the second bends, in some examples. Additionally, in some scenarios, the PCB may be positioned, as noted at 1108, following double bending of both flex interconnects.

At 1112, method 1100 may include connecting the flex interconnects to the one or more PCBs via connectors. As described with respect to FIGS. 6-10, each of the first and second flex interconnects may comprise a connector. The connectors may be affixed to or otherwise configured as a portion of first sections of each flex connector. The connectors may be positioned on an inner aspect of each of the first sections so as to face towards the one or more PCBs positioned between the first sections of the flex interconnects along the x-axis. In some embodiments, the one or more PCBs may include respective corresponding connectors for the connectors of the first and second flex interconnects to couple to. In other embodiments, the connectors of the first and second flex interconnects may be configured as edge board connectors, 90 degree board to board connectors, or other type of connector configured to connect directly to an edge of respective PCBs.

At 1114, method 1100 may include packing the transducer assembly into the probe housing. For example, the housing may be a layered construction including, for example, a plastic case exterior, a method shield, an acoustic insulator, and in some examples, may include a phase change chamber. It should be understood that additional components, such as heat dissipation devices, may be assembled as part of the transducer assembly and packaged into the probe housing.

The technical effect of the systems and methods provided herein is that contact between an acoustic module and one or more PCBs of a transducer assembly of an ultrasound probe while maintaining a reduced footprint of the probe in the elevation direction via one or more interconnects with a double bending configuration. Further, the double bending configuration may increase an amount of available surfaces for heat dissipation purposes, thereby reducing degradation to the components of the transducer assembly. The result of the systems and methods herein is a compact ultrasound probe configured for increased usability for various applications, including intercostal imaging, as well as increased user comfort and ergonomics.

The disclosure also provides support for an ultrasound probe, comprising: a housing, a transducer assembly positioned inside the housing, the transducer assembly comprising: an acoustic module, one or more printed circuit boards (PCBs), and one or more flex interconnects configured with an at least double bending configuration, wherein the one or more flex interconnects contact the acoustic module and the one or more PCBs. In a first example of the system, each of the one or more flex interconnects is partitioned into a first section, a second section, and a third section. In a second example of the system, optionally including the first example, each of the one or more flex interconnects comprises a first bend and a second bend, wherein the first bend transitions between the first section and the second section and the second bend transitions between the second section and the third section. In a third example of the system, optionally including one or both of the first and second examples, the one or more PCBs are positioned parallel to an azimuthal plane. In a fourth example of the system, optionally including one or more or each of the first through third examples, the first section of each of the one or more flex interconnects is positioned parallel to an azimuthal plane, the second section of each of the one or more flex interconnects is positioned parallel to an elevation plane, and the third section of each of the one or more flex interconnects is positioned parallel to the acoustic module. In a fifth example of the system, optionally including one or more or each of the first through fourth examples, the acoustic module is an electroacoustic module (EAM) comprising an acoustic stack and an application specific integrated circuit (ASIC) and wherein the one or more flex interconnects are positioned between the acoustic stack and the ASIC of the acoustic module. In a sixth example of the system, optionally including one or more or each of the first through fifth examples, the third section of each of the one or more flex interconnects is positioned between and in contact with the acoustic stack and the ASIC of the acoustic module.

The disclosure also provides support for a transducer assembly for an ultrasound probe, comprising: an acoustic module comprising an acoustic stack, at least one flex interconnect, each flex interconnect comprising a first section, a second section, and a third section, the first section of each of the at least one flex interconnects being coupled to the acoustic module, and one or more circuit boards, wherein the third section of each of the at least one flex interconnects is coupled to the one or more circuit boards, wherein each of the at least one flex interconnects comprise a first bend between the first section and the second section and a second bend between the second section and the third section. In a first example of the system, the first section of each of the at least one flex interconnects is positioned in contact with and parallel to the acoustic module and the second section of each of the at least one flex interconnects is positioned parallel to an elevation plane of the transducer assembly. In a second example of the system, optionally including the first example, the third section of each of the at least one flex interconnects comprises a connector to connect to one of the one or more circuit boards. In a third example of the system, optionally including one or both of the first and second examples, the connector of the third section of each of the at least one flex interconnects is configured to connect to a corresponding connector of a corresponding circuit board. In a fourth example of the system, optionally including one or more or each of the first through third examples, the connector of the third section of each of the at least one flex interconnects is configured to connect to an edge of a corresponding PCB. In a fifth example of the system, optionally including one or more or each of the first through fourth examples, each of the at least one flex interconnects is configured with an at least double bending configuration, comprising at least the first and second bends. In a sixth example of the system, optionally including one or more or each of the first through fifth examples, the first and second bends are 90 degree bends. In a seventh example of the system, optionally including one or more or each of the first through sixth examples, the first and second bends are less than or greater than 90 degree bends. In a eighth example of the system, optionally including one or more or each of the first through seventh examples, the first and second flex interconnects are configured to connect signals from the acoustic module in a first direction to the one or more circuit boards in a second direction.

The disclosure also provides support for a method, comprising: folding one or more flex interconnects of a transducer assembly of an ultrasound probe twice, and connecting the one or more flex interconnects to one or more printed circuit boards (PCBs) of the transducer assembly. In a first example of the method, the one or more flex interconnects contact at least one of an acoustic stack and an ASIC of an acoustic module. In a second example of the method, optionally including the first example, the one or more flex interconnects each comprise a flexible electrical interconnection device comprising conductive traces. In a third example of the method, optionally including one or both of the first and second examples, the one or more flex interconnects are each configured to transmit signals from the acoustic module to the one or more PCBs.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. An ultrasound probe, comprising:
- a housing;
- a transducer assembly positioned inside the housing, the transducer assembly comprising:
  - an acoustic module;
  - one or more printed circuit boards (PCBs); and
  - one or more flex interconnects, including a first flex interconnect and a second flex interconnect,
- wherein the first flex interconnect and the second flex interconnect are each configured with an at least double bending configuration,
- wherein each of the first flex interconnect and the second flex interconnect directly contacts the acoustic module and couples to the one or more PCBs via one or more connectors,
- wherein each of the first flex interconnect and the second flex interconnect is partitioned into a first section, a second section, and a third section, the second section positioned between the first section and the third section, and the first section and the third section each bending away in a direction opposite an external facing surface of the second section,
- wherein each of the first flex interconnect and the second flex interconnect comprises a first bend and a second bend,
- wherein the first bend transitions between the first section and the second section and the second bend transitions between the second section and the third section, and
- wherein the first section of each of the first flex interconnect and the second flex interconnect is positioned parallel to an azimuthal (x-z) plane, the second section of each of the first flex interconnect and the second flex interconnect is positioned parallel to an elevation (y-z) plane, and the third section of each of the first flex interconnect and the second flex interconnect is positioned parallel to the acoustic module, which is positioned parallel to an x-y plane.

2. The ultrasound probe of claim 1, wherein the acoustic module is an electroacoustic module (EAM) comprising an acoustic stack and an application specific integrated circuit (ASIC), and wherein the one or more flex interconnects are positioned between the acoustic stack and the ASIC of the acoustic module.

3. The ultrasound probe of claim 2, wherein the third section of each of the one or more flex interconnects is positioned between and in contact with the acoustic stack and the ASIC of the acoustic module.

4. A transducer assembly for an ultrasound probe, comprising:
- an acoustic module comprising an acoustic stack;
- a first flex interconnect and a second flex interconnect, each of the first and second flex interconnects comprising a first section, a second section, and a third section, the first section of each of the first and second flex interconnects being directly coupled to the acoustic module; and
- one or more circuit boards, wherein the third section of each of the first and second flex interconnects is coupled to the one or more circuit boards via a respective connector, wherein each of the first and second flex interconnects comprise a first bend between the first section and the second section and a second bend between the second section and the third section, wherein the first section of each of the first and second flex interconnects is positioned parallel to an azimuthal (x-z) plane, the second section of each of the first and second flex interconnects is positioned parallel to an elevation (y-z) plane, and the third section of each of the first and second flex interconnects is positioned parallel to the acoustic module, which is positioned parallel to an x-y plane, and wherein the first section and the second section are orthogonal to each other, and wherein the third section bends an inward direction.

5. The transducer assembly of claim 4, wherein the first section of each of the first and second flex interconnects is positioned in contact with and parallel to the acoustic module and the second section of each of the first and second flex interconnects is positioned parallel to an elevation plane of the transducer assembly.

6. The transducer assembly of claim 4, wherein the third section of each of the first and second flex interconnects comprises the respective connector to connect to one of the one or more circuit boards via a corresponding connector of a corresponding circuit board.

7. The transducer assembly of claim 4, wherein each of the first section, the second section, and the third section of each of the first and second flex interconnects are perpendicular to each of the other sections.

8. The transducer assembly of claim 6, wherein the connector of the third section of each of the first and second flex interconnects is configured to connect to an edge of a corresponding circuit board.

9. The transducer assembly of claim 4, wherein the first flex interconnect is coupled to a first circuit board of the one or more circuit boards via a first connector and the second flex interconnect is coupled to a second circuit board of the one or more circuit boards via a second connector.

10. The transducer assembly of claim 4, wherein the first and second bends are 90 degree bends.

11. The transducer assembly of claim 4, wherein the first and second bends are less than or greater than 90 degree bends.

12. The transducer assembly of claim 4, wherein the first and second flex interconnects are configured to connect signals from the acoustic module in a first direction to the one or more circuit boards in a second direction.

13. A method, comprising:

folding one or more flex interconnects of a transducer assembly of an ultrasound probe twice into a double bending configuration, wherein the one or more flex interconnects each comprise a first section, a second section, and a third section, wherein the folding includes bending the first section into the second section, and bending the second section into the third section to form a cuboidal shape, wherein when in the double bending configuration, the first section of each of the one or more flex interconnects is positioned parallel to an azimuthal (x-z) plane, the second section of each of the one or more flex interconnects is positioned parallel to an elevation (y-z) plane, and the third section of each of the one or more flex interconnects is positioned parallel to an acoustic module, which is positioned parallel to an x-y plane, wherein the one or more flex interconnects include a first flex interconnect and a second flex interconnect, wherein each of the first flex interconnect and the second flex interconnect comprises a first bend and a second bend, and wherein the first bend transitions between the first section and the second section and the second bend transitions between the second section and the third section; and connecting the one or more flex interconnects to one or more printed circuit boards (PCBs) of the transducer assembly.

14. The method of claim 13, wherein the one or more flex interconnects contact at least one of the acoustic stack and an ASIC of an acoustic module.

15. The method of claim 13, wherein the first section, the second section, and the third section form an L-shape prior to the folding.

16. The method of claim 14, wherein the one or more flex interconnects are each configured to transmit signals from the acoustic module to the one or more PCBs.

17. The ultrasound probe of claim 1, wherein the third section is oriented to be on top in the ultrasound probe.

18. The ultrasound probe of claim 1, wherein a width of the ultrasound probe extends along a length of the third section.

19. The ultrasound probe of claim 1, wherein the third section is more narrow in width as compared to both the first section and the second section, the width of the third section extending along an x-axis direction of the ultrasound probe.

20. The ultrasound probe of claim 1, wherein the first bend and the second bend are orthogonal relative to one another.

* * * * *